United States Patent [19]

Barnett

[11] Patent Number: 5,259,833
[45] Date of Patent: Nov. 9, 1993

[54] BACK BENDING MOTION LIMITING APPARATUS

[76] Inventor: Larry W. Barnett, 12 Nimrod Farm Rd., Weston, Conn. 06883

[21] Appl. No.: 945,098
[22] Filed: Sep. 15, 1992
[51] Int. Cl.5 .............................................. A61F 5/02
[52] U.S. Cl. ......................................... 602/19; 2/44; 2/45
[58] Field of Search .................. 2/44, 45; 602/19, 67; 128/78, 96.1; 224/153; 482/909

[56] References Cited

U.S. PATENT DOCUMENTS

| | | |
|---|---|---|
| 81,482 | 8/1868 | Eaton ..................... 2/45 X |
| 175,221 | 3/1876 | Whitmarsh ............. 2/45 X |
| 245,524 | 8/1881 | Lubin ........................ 2/45 |
| 401,223 | 4/1889 | Smith . |
| 654,173 | 7/1900 | Mendenhall . |
| 846,647 | 3/1907 | Craw et al. . |
| 1,104,150 | 7/1914 | Staab et al. . |
| 1,316,915 | 9/1919 | Meyer et al. ............ 602/19 |
| 2,906,260 | 9/1959 | Myers ....................... 602/19 |
| 3,338,236 | 8/1967 | McLeod .................. 2/44 X |
| 3,799,156 | 3/1974 | Gurkin . |
| 4,318,502 | 3/1982 | Lowe et al. ............. 224/153 |
| 4,608,716 | 9/1988 | Brumfield ................ 2/44 X |
| 4,829,989 | 5/1989 | Deamer et al. . |
| 4,938,476 | 7/1990 | Brunelle et al. ........ 462/909 X |
| 5,040,524 | 8/1991 | Votel et al. . |

OTHER PUBLICATIONS

The Marmot Mountain Works Catalog, Fall-Winter 1984, p. 20.

Primary Examiner—Richard J. Apley
Assistant Examiner—Beverly A. Meindl
Attorney, Agent, or Firm—St. Onge Steward Johnston & Reens

[57] ABSTRACT

A harness for minimizing possible back injury from excessive or improper bending and lifting includes a flexible back strap, a pair of flexible shoulder straps attached to the back strap, and an anchor holding the back strap to the wearer's pants. The pair of shoulder straps fit over the wearer's shoulders and below the wearer's shoulder blades so that the wearer has free movement of his scapula and arms. The anchor and pants restrain back bending by the wearer beyond a predetermined maximum angle by the interference of the wearer's pants with the anatomic structure of the wearer's groin.

23 Claims, 6 Drawing Sheets

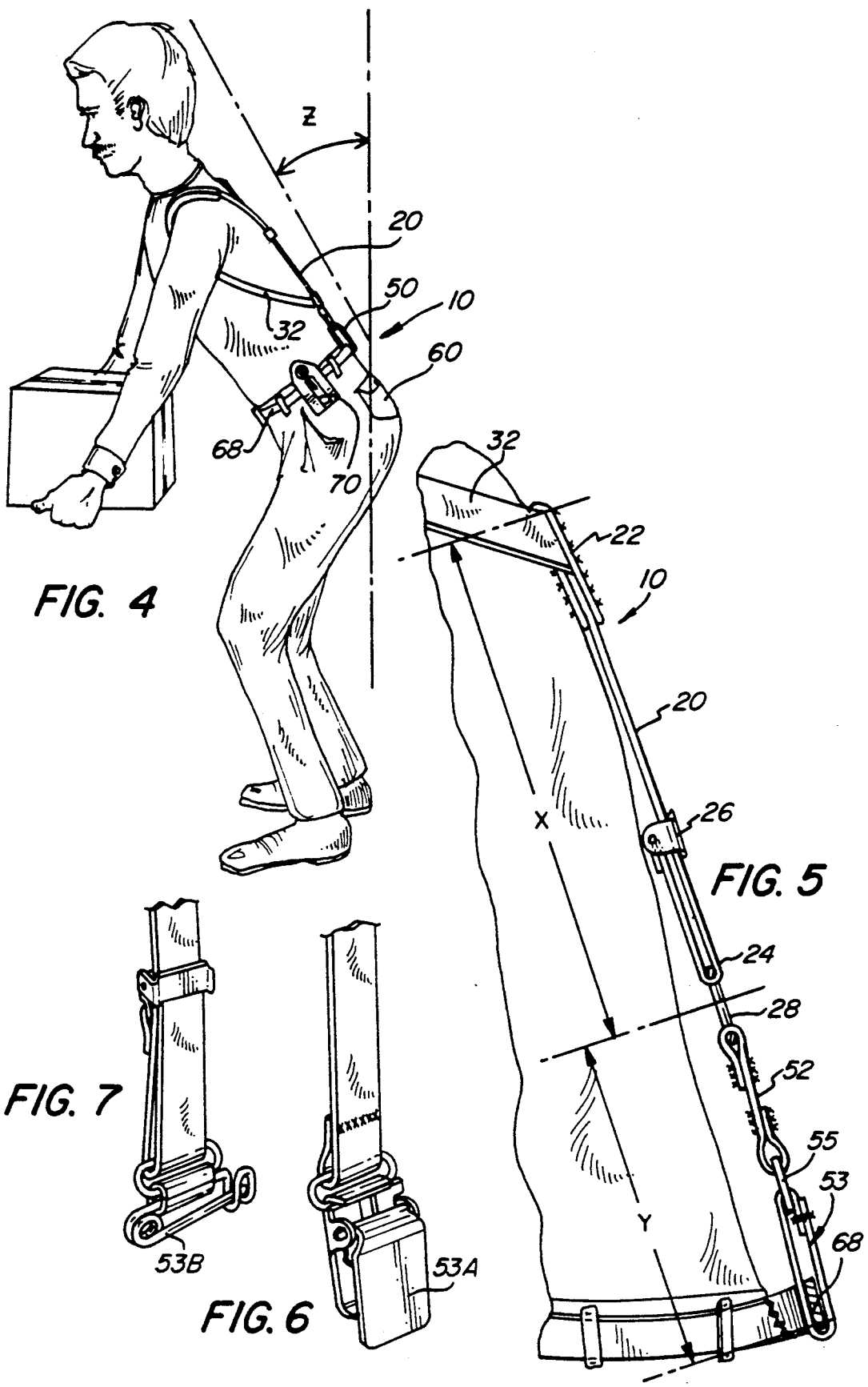

BACK BENDING MOTION LIMITING APPARATUS

BACKGROUND OF THE INVENTION (1) Field of the Invention

The present invention relates to a harness apparatus for limiting movement of the human torso to prevent back injury.

(2) Description of the Prior Art

Various types of back supports have been described that wrap tightly around the abdomen and lumbar regions of the body to provide support for lifting and other physical exertion. One such device is disclosed in U.S. Pat. No. 5,040,524. However, these devices do not provide a limit on back bending movement of the upper torso, so that excessive, improper bending can still take place during heavy lifting. Other supporting braces have also been known and used to provide support for manual laborers such as disclosed in U.S. Pat. Nos. 401,223 and 654,173. However, these devices have generally restricted free shoulder and arm movement by straps or bands that are placed tightly against the shoulderblades and have relied on leg belts to support the devices worn on the upper torso. The defect of limited and restrained shoulder movement is also seen in the appliance disclosed in U.S. Pat. No. 1,104,150 which consists of a wooden board affixed to a chair; a pupil is restrained with his back to the board by leather straps and buckles.

In sum, the prior art has not provided a back bending motion limiting harness that is comfortable to wear, which leaves the shoulders and arms free to move, and which limits the angle of the back relative to the waist to prevent back injury by preventing the back from overextending beyond a predetermined limit.

SUMMARY OF THE INVENTION

A back bending motion limiting harness for back safety of a wearer in accordance with one embodiment of the invention comprises a flexible centrally located back strap, a pair of flexible shoulder straps attached to the center back strap, and an anchor holding the center back strap to the wearer's pants.

The back strap has an upper end and a lower portion, and is preferably provided with a length adjustment buckle to accommodate different size wearers and to set the predetermined maximum angle of forward bending of the wearer.

The pair of shoulder straps are connected at the upper end of the back strap and extend upwardly and angularly away from the back strap over the wearer's shoulders and then backwardly below the wearer's shoulder blades to connect with the lower portion of the back strap. The back strap has a sufficient length such that the lower connections between the shoulder straps and the back strap are located beneath the shoulder blades to prevent the shoulder straps from impeding free movement of the wearer's scapula and the wearer's arms. Preferably, the shoulder straps are provided with length adjustment buckles to accommodate different size wearers and to set the predetermined maximum angle of forward bending of the wearer, and preferably have quick connect buckles permitting quick putting on and removal of the harness.

The anchor for the back strap secures the harness to a pair of pants and restrains forward back bending by the wearer beyond a predetermined maximum angle by the interference of the wearer's pants with the anatomic structure of the wearer's groin. The interference of the pants with the groin area limits the forward back bending of the wearer by the effect of the shoulder straps acting on the wearer's shoulders.

The anchor for the back strap preferably comprises an anchor strap and a coupling; various embodiments of the coupling include: a loop sized and located to be retained by a belt, a clip to be secured to the wearer's pants, a pin to pin the strap to the wearer's pants, and a permanent fastening to a pair of shorts. In another embodiment, there are two securing devices extending downwardly and apart to limit twisting of the wearer's torso.

The length of the back strap to the anchor strap is between about 1.6:1 to about 6.0:1, preferably about 2.4 to 4.2; also, preferably the shoulder straps meet the back strap at an angle between about 80 degrees to about 50 degrees.

Further objects and details of the present invention can be seen from the accompanying drawings and detailed description of the preferred embodiment set forth below.

BRIEF DESCRIPTION OF THE DRAWINGS

FIG. 4 is a side perspective view showing the operation of the back bending motion limiting harness of FIG. 1 to prevent excessive bending during lifting of an object.

FIG. 5 is a detail cross-sectional view of a portion of the back bending motion limiting harness as seen in FIG. 4.

FIG. 6 is an alternative clip embodiment of an anchor of a back bending motion limiting harness.

FIG. 7 is an alternative pin embodiment of an anchor of a back bending motion limiting harness.

DETAILED DESCRIPTION OF THE PREFERRED EMBODIMENT

Figure 1:
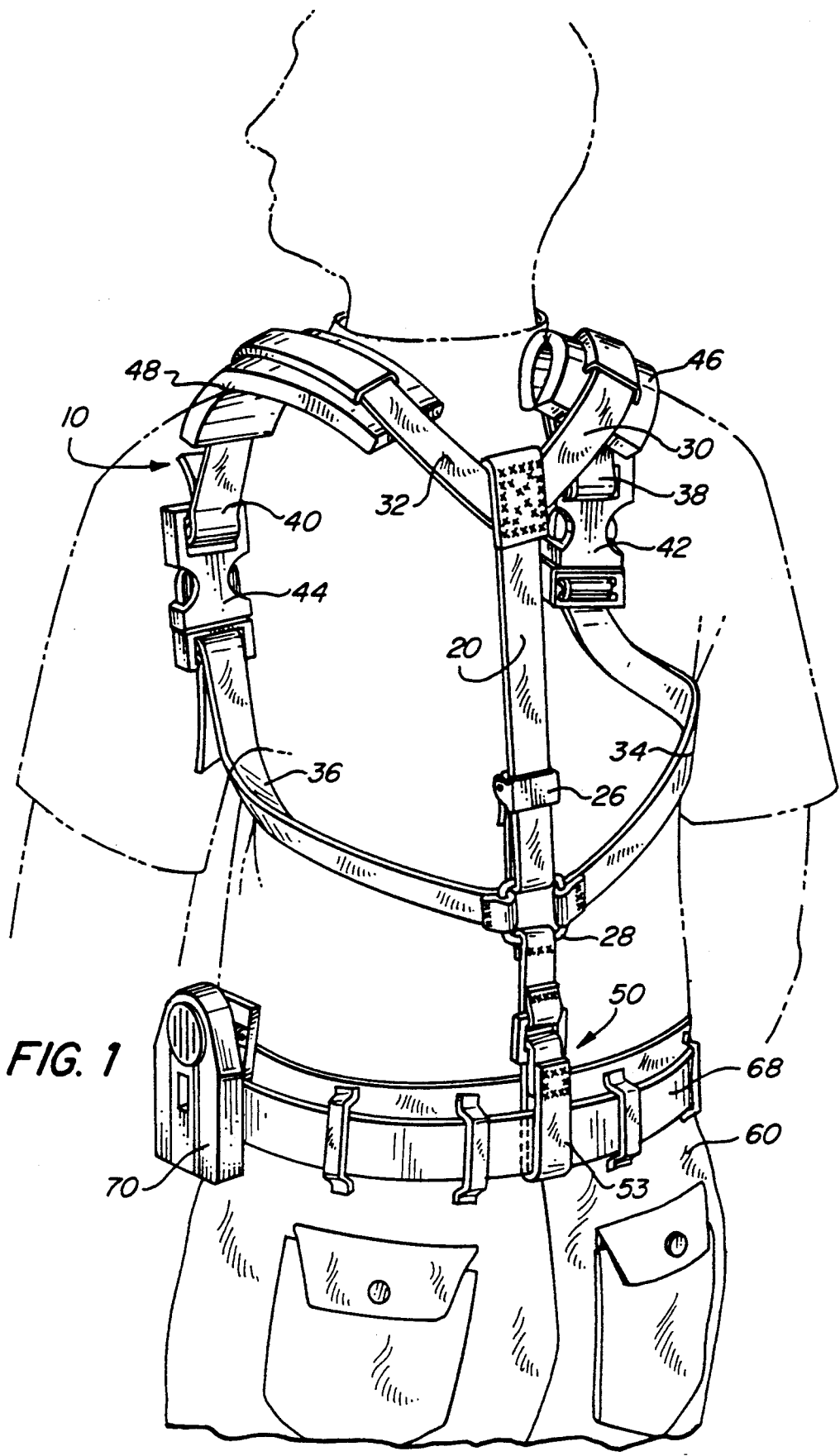
FIG. 1 is a rear perspective view of one embodiment of a back bending motion limiting harness for back safety in its intended use.
Figures 2, 3:
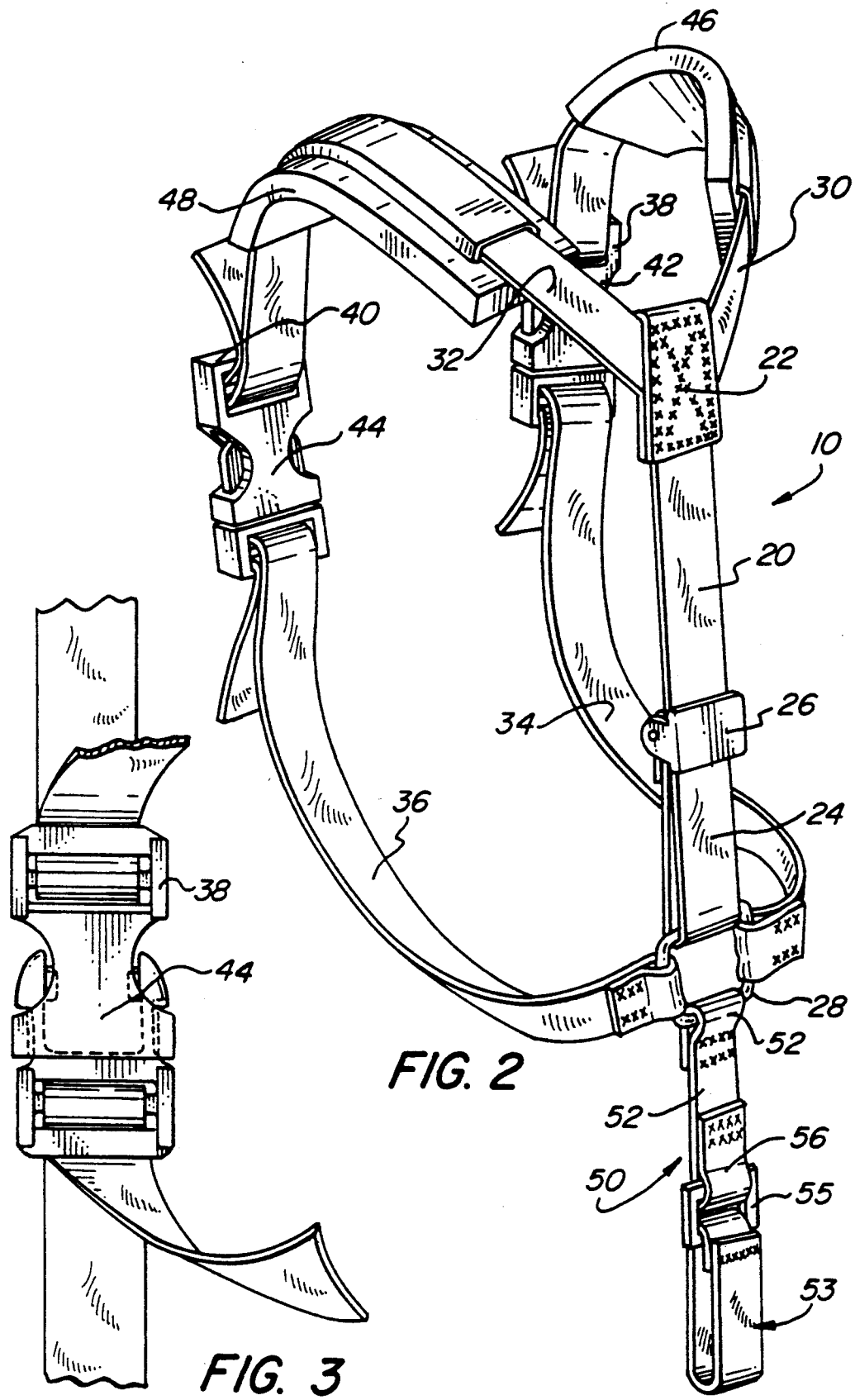
FIG. 2 is a rear perspective view of the back bending motion limiting harness of FIG. 1.
FIG. 3 is a front elevation view of a quick connect buckle used in the back bending motion limiting harness of FIG. 1.

Referring now to FIGS. 1-10, where like numbers in the Figures indicate like elements, the present invention provides a back bending motion limiting harness 10 that comprises a flexible generally centrally located back strap 20, a pair of flexible shoulder straps 30 and 32 attached to the back strap 20, and an anchor 50 holding the back strap 20 to the wearer's pants 60.

The back strap 20 is preferably a single strap although it may comprise multiple strap elements, and has an upper end 22 and a lower portion 24, and is preferably provided with a length adjustment buckle 26. Length adjustment buckle 26 permits adjustment of the length of the back strap 20 to size harness 10 for wearers having different torso length and width sizes. Buckle 26 also is used to adjust the maximum angle of forward bending of the wearer to a predetermined maximum.

The back strap 20 may be made from a variety of materials and may include woven fabric, leather and leather-like materials. Preferably, the back strap is a material with limited or non-stretch characteristics.

The pair of shoulder straps 30 and 32 are connected at the upper end 22 of the back strap 20 and extend upwardly and angularly away from the back strap 20 so that they will fit over the wearer's shoulders. The straps 30 and 32 then extend backwardly under the wearer's arms and below the wearer's shoulder blades to connect with a connector element 28 affixed to the lower portion 24 of the back strap 20. The back strap 20 has a sufficient length such that the sections 34 and 36 of the shoulder straps 30 and 32 which extend under the wearer's arms and shoulder blades do not impede free movement of the wearer's scapula and the wearer's shoulders and arms. Preferably, the shoulder straps 30 and 32 are provided with length adjustment clips 38 and 40 respectively to accommodate different size wearers and to set the predetermined maximum angle of forward bending of the wearer. Most preferably, the shoulder straps 30 and 32 are provided with quick connect buckles 42 and 44 permitting quick mounting and removal of the harness 10.

Shoulder straps 30 and 32 are preferably provided with pads 46 and 48 to provide additional comfort in use.

The back strap 20 is secured by an anchor 50 to to a pair of pants 60. When the wearer bends improperly, the interference of the wearer's pants 60 with the anatomic structure of the wearer's groin anchors the harness 10 so that it restrains forward back bending by the wearer beyond a predetermined maximum angle Z as shown in FIG. 4. Such restraint arises by the limitation of movement of the pants in the sagittal plane of the body as they are caught by the groin area (the sagittal plane is a plane which passes through the long axis of the body), as well as by the limitation of movement of the material in the front of the pants legs in the coronal plane (the coronal plane is a plane which passes perpendicularly to the sagittal plane). In other words, bending is restrained when the pants 60 are caught in the gluteal crease.

Bending is also restrained by virtue of the anchoring effect of the pants legs which enclose the wearer's legs and have a limited range of movement. The interference of the pants 60 with the wearer's anatomy anchors the shoulder straps 30 and 32. It is to be appreciated that in order for the invention to be most effective, the wearer's pants 60 should be reasonably well fitted in the wearer's groin area without a substantial amount of loose fabric that would be too slack to provide the desired restraint. However, it is possible to accommodate loose fitting pants by proper adjustment of the length adjustment buckle 26 to shorten the back strap 20.

In the preferred embodiment, the anchor 50 consists of an anchor strap and a coupling. Anchor strap 52 is preferably secured at one upper end 54 to the connector element 28. The coupling is affixed to the anchor strap lower end 56.

Figure 8:
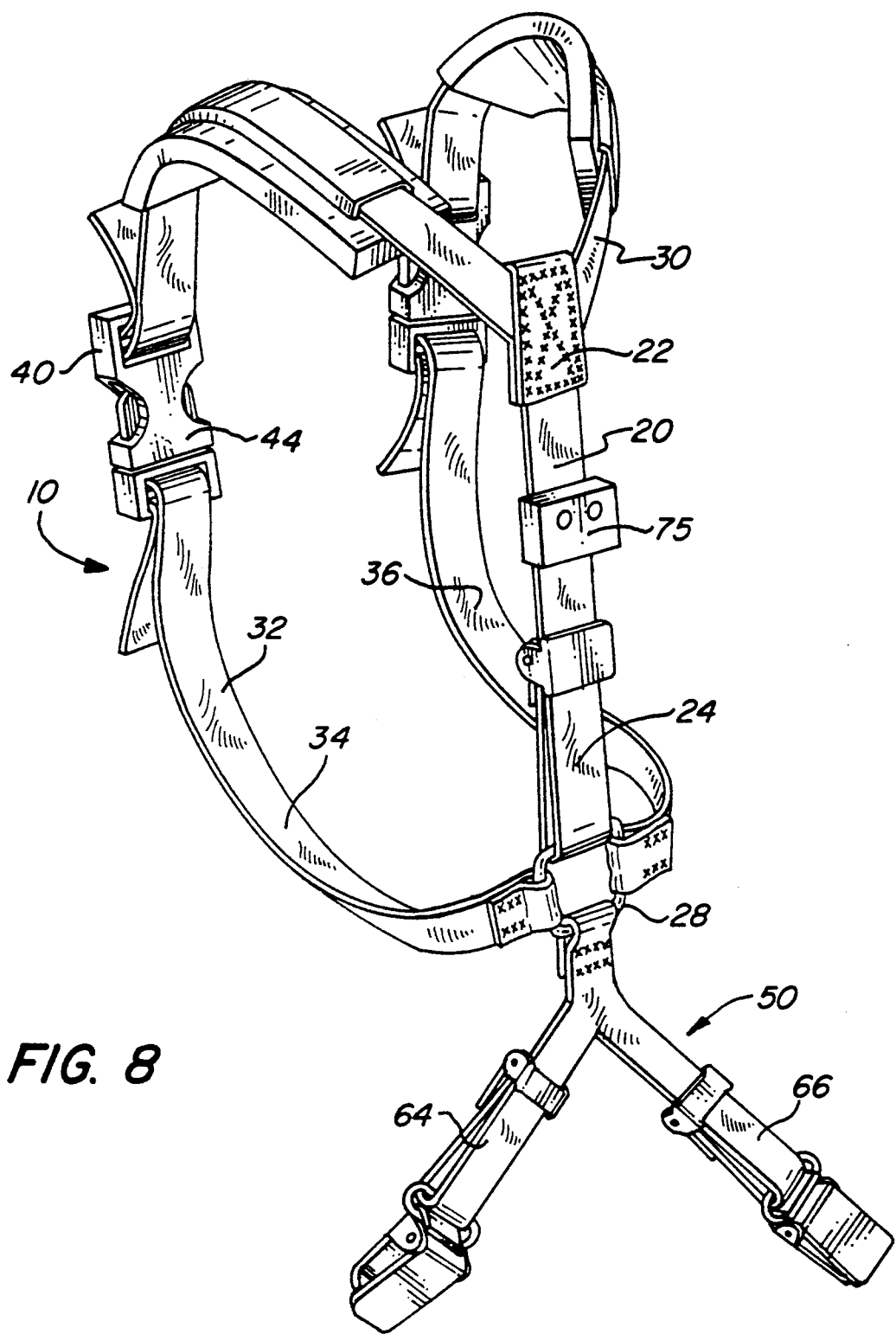
FIG. 8 is an alternative double clip embodiment of an anchor of a back bending motion limiting harness.
Figure 9:
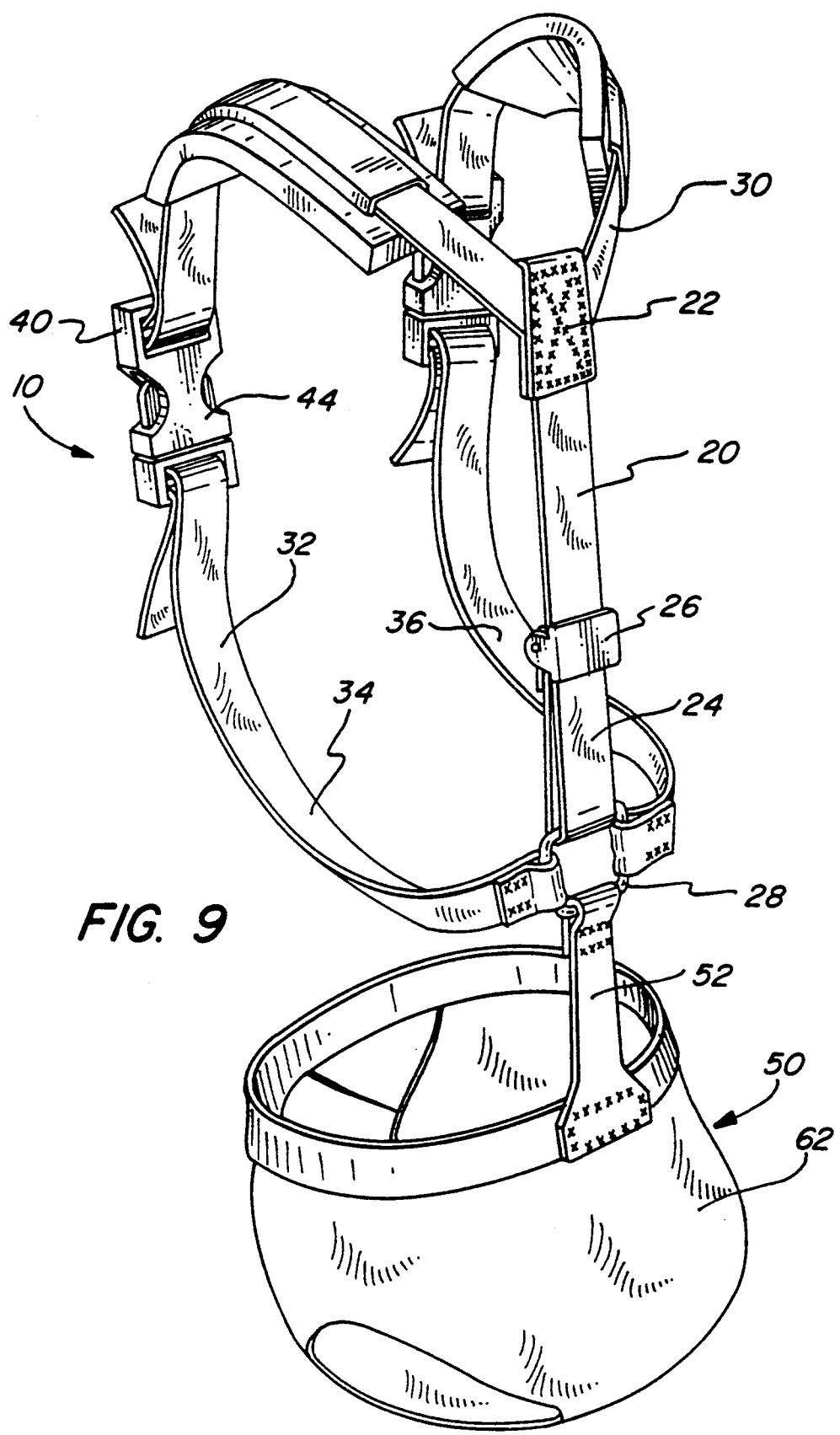
FIG. 9 is an alternative shorts embodiment of an anchor of a back bending motion limiting harness.

The coupling for the back strap may take a variety of alternate embodiments as shown in FIGS. 2, 6, 7, 8, and 9. In FIGS. 1, 2, 4, and 5, the coupling is a loop 53 sized and located to be retained by a belt 68 worn by the wearer in a conventional manner as part of the wearer's pants 60. The coupling loop 53 is retained to the anchor strap 52 by a connector ring 55. In FIG. 6, the coupling is a clip 53A adapted to be clipped to the upper edge of the fabric of the wearer's pants 60. In FIG. 7, the coupling is a pin 53B adapted to be pinned to the fabric of the wearer's pants 60. In FIG. 9, the coupling and anchor are provided by directly securing the back strap 20 to a pair of shorts 62 by sewing or other fastenings.

In another embodiment, shown in FIG. 8, there are two securing devices such as the two straps 64 and 66 each with a clip extending downwardly and apart to limit twisting of the wearer's torso.

Figure 10:
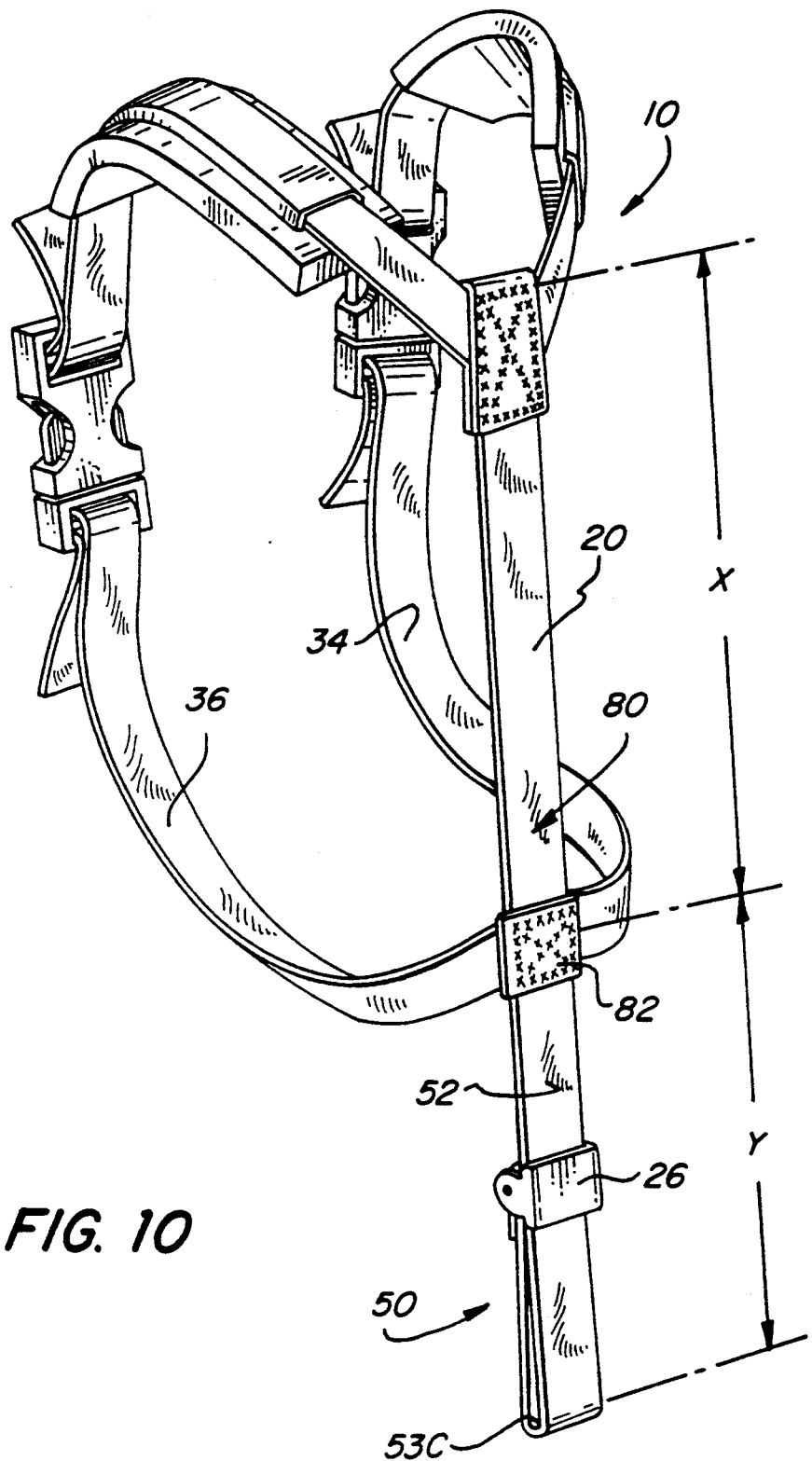
FIG. 10 is a rear perspective view of another embodiment of a back bending motion limiting harness.

It is to be appreciated that the functions of the back strap and anchor can be combined in one component and need not comprise separate components. Referring now to FIG. 10, it can be seen that there is a single strap 80 that has a back strap section 20, an anchor section 50 comprising an anchor strap section 52 that also acts as a coupling loop 53C by the looping of the lower end of the anchor strap section of the single strap 80. It is to be understood that "back strap" as used herein can thus be defined as the portion of the harness extending between the upper and lower ends of the shoulder straps, and that "anchor strap" as used herein can be defined as any portion of the harness extending downwardly from the lower connection between the back strap and the shoulder straps.

By way of further example, the shoulder straps as seen in FIG. 10 might connect to a sliding apparatus 82 that can slide up and down the back strap and anchor strap and be secured at a selected location. In such case, the portions of the harness which are considered the back strap and anchor strap can vary in length. Thus it is to be appreciated that the invention is not limited to fixed straps as shown in some of the drawings.

The effectiveness of the harness is its ability to allow free movement of the wearer's arms, shoulders and scapula while restraining forward bending beyond a preset limit. This is obtained by making the back strap 20 sufficiently long and the anchor strap 52 sufficiently short such that the straps are located in the desired physiological location where they do not interfere with the free movement of the body. When harness 10 is worn, it is preferable for the shoulder straps 30 and 32 to have lower connections with the back strap 20 at an angle between about 80 degrees to about 50 degrees. The preferred angles also help to insure that the shoulder straps 30 and 32 pass below the scapula and do not obstruct their free movement. The upper connection between the upper end 22 of the back strap and the shoulder straps 30 and 32 is also important. This upper connection should not be so high as to impede the neck muscles, yet must also be sufficiently high so as to permit free movement of the scapula.

The invention may also be defined by the relative lengths of the back strap and anchor strap portions of the harness. In particular, to obtain the desired location of the lower connection between the shoulder straps and the back strap below the scapula, the relative lengths of the back strap and anchor strap fall within a ceratin range of desired ratios. Referring now to FIG. 5, the ratio of the length X of the back strap 20 to the length Y of the anchor 50 should be in a range of between about 1.6:1 to about 6.0:1, depending on the size of the wearer. Typically, with a larger, taller person, the length of the back strap will be longer that with a shorter person, and length ratios of between 3:1 to 6:1 will be used, while with shorter persons, length ratios of about 1:6 to about 3.5:1 will be used. It is desired to have the ratio in this range to insure that the shoulder straps 30 and 32 pass below the scapula and do not obstruct their free movement. In one preferred embodiment, the ratio of the back strap to anchor is about 2.4:1 to about 4.2:1.

It is to be appreciated that the relative lengths of the back strap and anchor are dependent on variables such as the belt width, the trouser styling (i.e. the height of the trousers from crotch to waist) as well as the physical structure of the wearer. Accordingly, the length Y of the anchor strap and length X of the back strap may vary, and there terminating endpoints will also vary.

The present invention can be worn and the proper angle of maximum bending determined and the proper lengths of the back strap 20 and the shoulder straps adjusted using a torso attitude sensor to detect the bending angle of the wearer. Preferably, the straps are adjusted to restrain bending beyond a maximum back bending angle using the device described in my copending application entitled "Torso Attitude Sensor", filed Aug. 21, 1991 and pending as application Ser. No. 07/748,275, the entire disclosure of which is hereby incorporated by reference.

A torso attitude sensor device 70 may be worn in conjunction with the harness 10 to alert the wearer or an observer of improper bending or torso attitudes. The device 70 would typically include an angle-sensitive mercury switch to alert the wearer when the angle of torso bending exceeds a certain limit. Such a device should include a counter to count the number of improper bends during a counting period. A display to indicate improper bends preferably would include an optical signal, for example, a green light indicating proper posture and a red light indicating improper bending or posture. A simpler version of the sensor would simply have a red light which would be activated on improper bending. Such a simple version might be desirable as no on-off switch would be needed and it would draw power only when activated, consequently reducing cost and avoiding the possibility that a wearer might purposely turn off the sensor.

An audible sound generator might also be incorporated to broadcast a tone to alert the wearer or an observer of improper bending.

An alternative embodiment of a sensor would incorporate stretch or tension sensing equipment that would detect when excessive stress was placed on the back strap of the harness by bending of the wearer and would alert the wearer of such excessive stress. Such an alternative embodiment is shown at 75 in FIG. 8.

The present invention provides a harness especially suited for preventing back injury by acting as a restraint against excessive torso flexion, and forces the wearer to bend the knees to perform proper lifting. The harness is a bending restraint that nevertheless permits the free movement of arms, shoulders and scapula, in contrast to various prior art devices that unacceptably restrained the free movement of the scapula, shoulders and arms. Since the harness does not act on the torso until the wearer attempts to bend improperly, it is comfortable, and this makes it more effective, since the wearer will not be tempted to remove the harness.

It is to be appreciated that the harness 10 is unique in its use of an anchor solely in the rear of the torso. This reduces the problem of the wearer's shoulders being able to rotate within the harness to avoid any restraint on bending that may occur in prior art devices. The harness 10 is an effective restraint on forward bending.

It is to be appreciated that the foregoing is illustrative and not limiting of the invention, and that various changes and modifications to the preferred embodiments described above will be apparent to those skilled in the art. Such changes and modifications can be made without departing from the spirit and scope of the present invention, and it is therefore intended that such changes and modifications be covered by the following claims.

I claim:

1. A back bending motion limiting harness for back safety of a wearer, comprising:

a flexible generally centrally located back strap formed of a substantially non-stretchable material having an upper end and a lower portion;

a pair of flexible shoulder straps formed of a substantially non-stretchable material, said shoulder straps each having one end connected to the upper end of said back strap, said shoulder straps extending upwardly and angularly away from the upper end of said back strap to extend forwardly and downwardly over the wearer's shoulders and then backwardly below the wearer's scapula to allow free movement of the wearer's arms while other ends of said shoulder straps effectively connect with said lower portion of said back strap, the effective connections between the ends of said shoulder straps and the back strap being so located and the lengths of said back strap and shoulder straps being so selected so as to prevent said shoulder straps and back strap from impeding free movement of the wearer's scapula while setting a predetermined maximum forward bending angle for the wearer; and means formed of a substantially non-stretchable material and having a length selected for anchoring said lower portion of said back strap to an upper part of the back of pants of the wearer, whereby forward back bending by the wearer beyond said predetermined maximum angle is restrained by the anchored shoulder straps acting on the wearer's shoulders.

2. A back bending motion limiting harness in accordance with claim 1, further comprising: length adjustment means provided in said back strap to accommodate differently sized wearers and to set the predetermined maximum angle of forward bending of the wearer.

3. A back bending motion limiting harness in accordance with claim 2, further comprising: length adjustment means provided in each said shoulder strap to accommodate differently sized wearers.

4. A back bending motion limiting harness in accordance with claim 1, wherein said means for anchoring comprises an apparatus selected from the group consisting of: a loop secured to the lower portion of the back strap, said loop being sized and located to receive and be secured by a wearer's belt, a clip effectively extending from a pin secured to the lower portion of said back strap, and a pair of shorts wearable by the wearer and having said lower portion of said back strap secured thereto.

5. A back bending motion limiting harness in accordance with claim 1, wherein said means for anchoring comprise first and second non-stretchable strap securing devices extending downwardly at an angle from the lower portion of said back strap to the back of the wearer's pants at spaced apart locations selected to limit twisting of the wearer's torso.

6. A back bending motion limiting harness in accordance with claim 1, wherein said flexible shoulder straps encircle said wearer's shoulder without a connection to said pants of the wearer except for said anchoring means.

7. A back bending motion limiting harness in accordance with claim 2, further comprising sensor means for wearing in conjunction with said harness and for generating a count of the number of improper bending postures of the wearer when said length adjustment means enables the wearer to bend beyond a predetermined maximum forward bending angle.

8. A back bending motion limiting harness for back safety of a wearer, comprising:
 a flexible generally centrally located back strap formed of a substantially non-stretchable material having an upper end and a lower portion;
 a pair of flexible shoulder straps formed of a substantially non-stretchable material, said shoulder straps being connected at the upper end of said back strap to extend upwardly and angularly away from said back strap and forwardly and downwardly over the wearer's shoulders and then backwardly below the wearer's scapula to allow free movement of the wearer's arms, means for connecting shoulder straps that pass below the wearer's scapula to said lower portion of said back strap, said back strap having a sufficient length such that upper and lower effective connections between said shoulder straps and said back strap are located to prevent said shoulder straps from impeding free movement of the wearer's scapula; and
 substantially non-stretchable means for anchoring said lower portion of said back strap to an upper part of the back of a groin engaging garment of the wearer, to restrain forward back bending by the wearer beyond a predetermined maximum angle when an interference of the wearer's garment with the anatomic structure of the wearer's body arises from a pulling of the shoulder straps attributable to a forward back bending by the wearer.

9. A back bending motion limiting harness in accordance with claim 8, wherein said means for anchoring comprises an apparatus selected from the group consisting of: a loop secured to the lower portion of the back strap, said loop being sized and located to receive and be secured by a wearer's belt, a clip effectively extending from the lower portion of said back strap, a pin secured to the lower portion of said back strap, and a pair of shorts wearable by the wearer and having said lower portion of said back strap secured thereto.

10. A back bending motion limiting harness in accordance with claim 8, and further including means for adjusting the length of the back strap to select the maximum forward bending angle.

11. A back bending motion limiting harness in accordance with claim 9, further comprising: length adjustment buckles provide in said shoulder straps to accommodate differently sized wearers and to set the predetermined maximum forward bending angle of the wearer.

12. A back bending motion limiting harness in accordance with claim 8, wherein the ratio of the length of said back strap to the length of the anchoring means is between about 1.6:1 to about 6.0:1.

13. A back bending motion limiting harness in accordance with claim 12, wherein said ratio is in the range of about 2.4:1 to about 4.2:1.

14. A back bending motion limiting harness in accordance with claim 8, wherein an angle is formed between said shoulder straps and the lower portion of said back strap, said angle being between about 80 degrees to about 50 degrees.

15. A back bending motion limiting harness in accordance with claim 2, further comprising sensor means for wearing in conjunction with said harness and for generating a count of the number of improper bending postures of the wearer when said length adjustment means enables the wearer to bend beyond the predetermined maximum forward bending angle.

16. A back bending motion limiting harness for back safety of a wearer, essentially consisting of:
 a connector element;
 a flexible, generally centrally located substantially non-stretchable back strap having an upper end and a lower portion, said lower portion being secured to said connector element;
 a pair of flexible shoulder straps formed of substantially non-stretchable material, said shoulder straps being connected to the upper end of said back strap to extend upwardly and angularly away from said back strap over the wearer's shoulders and to extend forwardly and downwardly over the wearer's shoulders and then backwardly below the wearer's shoulder blades to connect to said connector element in said lower portion of said back strap to thereby allow free movement of the wearer's arms, said back strap having a sufficient length such that said connections between said shoulder straps and said connector element and the upper end of the back strap are located to prevent said shoulder straps from impeding free movement of the wearer's shoulder blades, said shoulder straps and back strap being provided with length adjustment means to accommodate differently sized wearers and to set a predetermined maximum forward bending angle of the wearer;
 said shoulder straps further having quick connect/disconnect means for the convenient use and removal of said harness;
 an anchor strap formed of a substantially non-stretchable material and having one end connected to said connector element and extending downwardly therefrom; and
 coupling means, connected to a downward end of the anchor strap, for anchoring said anchor strap to a rear portion of a pants of the wearer, whereby forward back bending by the wearer beyond said predetermined maximum angle is restrained by an interference of the wearer's pants with the anatomic structure of the wearer's groin when the shoulder straps act on the wearer's shoulders as a result of forward bending.

17. A back bending motion limiting harness in accordance with claim 16, wherein said coupling for anchoring comprises an apparatus selected from the group consisting of: a loop formed by said anchor strap and sized to receive and be secured by a wearer's belt secured to the wearer's pants; a clip sized to engage the wearer's pants; and a pin.

18. A back bending motion limiting harness in accordance with claim 16, wherein said coupling means comprises first and second non-stretchable strap securing devices extending downwardly at an angle from the connector element, to be secured to a wearer's pants at spaced apart locations selected to limit twisting of the wearer's torso.

19. A back bending motion limiting harness in accordance with claim 16, wherein said back strap has a length, and said anchor strap and coupling have a combined length, and the ratio of the length of said back strap to the combined length of the anchor strap and coupling is between about 1.6:1 to about 6.0:1.

20. A back bending motion limiting harness in accordance with claim 19, wherein said ratio is in the range of about 2.4:1 to about 4.2:1.

21. A back bending motion limiting harness in accordance with claim 16, wherein there is an angle between said shoulder straps and said back strap where said shoulder and back straps are joined at the connector element, said angle being between about 80 degrees to about 50 degrees.

22. A back bending motion limiting harness in accordance with claim 16, further comprising a torso attitude sensor for wearing in conjunction with said harness and providing a count of the number of improper bending postures by the wearer and, wherein said sensor may be used to determine the optimum length of said back strap for said maximum forward bending angle.

23. A back bending motion limiting harness in accordance with claim 22, wherein said sensor includes a visible counter, which counts the number of times the wearer bends beyond the maximum forward bending angle.

* * * * *